United States Patent [19]
Goldstein et al.

[11] Patent Number: 5,585,352
[45] Date of Patent: Dec. 17, 1996

[54] METHOD OF TREATING SEPTIC SHOCK USING THYMOSIN-α 1

[75] Inventors: Allan J. Goldstein, Bethesda, Md.; Mirela O. Fagarasan, Washington, D.C.

[73] Assignee: The George Washington University Medical Center, Washington, D.C.

[21] Appl. No.: 258,177

[22] Filed: Jun. 10, 1994

Related U.S. Application Data

[63] Continuation-in-part of Ser. No. 132,859, Oct. 7, 1993, abandoned.

[51] Int. Cl.⁶ .............................. A61K 38/00; C07K 5/00; C07K 7/00; C07K 17/00
[52] U.S. Cl. .............................. 514/12; 530/324; 530/301
[58] Field of Search ..................................... 530/324, 301; 514/12

[56] References Cited

U.S. PATENT DOCUMENTS

| | | | |
|---|---|---|---|
| 4,079,127 | 3/1978 | Goldstein et al. | 424/177 |
| 4,297,276 | 10/1981 | Golstein et al. | |
| 5,055,447 | 10/1991 | Palladino et al. | 514/12 |

OTHER PUBLICATIONS

Cross et al, Infection and Immunity vol. 61 p. 2741 (1993).
Fitzer–Schiller, Washington Post, Jan. 19, 1993 p. D3.
Biotechnology Newswatch, Aug. 1, 1994 pp. 1 and 4.
Ishitsuka et al., "Protective Activity of Thymosin Against Opportunistic Infections in Animal Models," *Cancer Immunology Immunotherapy*, 14:3, pp. 145–150 (Mar. 1983).
Sanders et al., "Thymosin $\beta_4$ (Fx peptide) is a potent regulator of actin polymerization in living cells", *Proc. Natl. Acad. Sci. USA*, 89:10, pp. 4678–4682, May 15, 1992.
Ashkenazi et al., "Protection against endotoxic shock by a tumor recrosis factor receptor immunoadhesin", *Proc. Natl. Acad. Sci. USA*, 88:23, pp. 10535–10539, Dec. 1, 1991.
Watt et al., "Alterations in plasma levels and complexing of Gc (vitamin D–binding protein) in rats with endotoxic shock", *Biological Abstracts*, 88:7, Abstract No. 75029, 1989 (*Circ Shock*, 28:3, pp. 279–292, 1989).
Sawada, Shuzo, et al., "Protection against Infection with *Pseudomonas aeruginosa* by Passive Transfer of Monoclonal Antibodies to Lipopolysaccharides and Outer Membrane Proteins," *J. of Inf. Diseases*, 150:4 (Oct. 1984) p. 570.
Low, Teresa L. K., et al., "Thymosins: structure, function and therapeutic applications," *Thymus* 6, pp. 27 et seq. (1984).
Teng, Nelson N. H., et al., "Protection against Gram–negative bacteremia and endotoxemia with human monoclonal IgM antibodies," *Proc. Natl. Acad. Sci.*, vol. 82, pp. 1790–1794 (Mar. 1985).
Webster's Third New International Dictionary, p. 1798 (1986).
Dorland's Illustrated Medical Dictionary, 26th ed., p. 1026.
Baumgartner, J. D., et al., "Asociation between Protective Efficacy of Anti–Lipopolysaccharide (LPS) Antibodies and Suppression of LPS–Induced Tumor Necrosis Facto α and Interleukin 6," *J. Exp. Med.*, 171:889–896 (Mar. 1990).
Safer, Daniel, et al., "Thymosin $\beta_4$ and Fx, an Actin–sequestering Peptide, Are Indistinguishable," *J. of Biol. Chem.*, vol. 266, No. 7, pp. 4029–4032 (Mar. 1991).
Lee, William M., et al., "The Extracellular Actin–Scavenger System and Actin Toxicity," *New England J. of Med.*, vol. 326, No. 20, pp. 1335–1341 (May. 14, 1992).

*Primary Examiner*—Marian C. Knode
*Assistant Examiner*—Sheela J. Huff
*Attorney, Agent, or Firm*—Rothwell, Figg, Ernst & Kurz

[57] ABSTRACT

A method of reducing toxicity of endotoxin in a mammal including the administration of an endotoxin-reducing effective amount of $T\alpha_1$ to the mammal.

4 Claims, No Drawings

METHOD OF TREATING SEPTIC SHOCK USING THYMOSIN-α 1

BACKGROUND OF THE INVENTION

CROSS-REFERENCE TO RELATED APPLICATION

This application is a continuation-in-part of U.S. patent application Ser. No. 08/132,859, filed Oct. 7, 1993, abandoned.

FIELD OF THE INVENTION

The present invention relates to a method of treating septic shock in mammals.

DESCRIPTION OF BACKGROUND ART

Thymosin $\alpha_1$ ("T$\alpha_1$") is a peptide originally derived from the Thymus gland, which has been reported as containing 28 amino acids. Amino acid sequence information on T$\alpha_1$ is disclosed in U.S. Pat. No. 4,079,127, incorporated herein by reference.

T$\alpha_1$ is an immune system modulator which heretofore has been reported as being useful, inter alia, in the treatment of lung cancer, Hepatitis B and Hepatitis C.

Septic shock is a condition in which infection is widely disseminated in many areas of the body, the infection generally being disseminated through the blood from one tissue to another and causing extensive damage. Septic shock can occur with numerous medical conditions, including (1) peritonitis caused by the spread of infection from the uterus and fallopian tubes; (2) peritonitis resulting from rupture of the gut, sometimes caused by intestinal disease or wounds; (3) generalized infection resulting from spread of a simple infection; (4) generalized gangrenous infection resulting specifically from gas gangrene bacilli; and (5) infection spreading into the blood from the kidney or urinary tract. Septic shock is of critical concern from a clinical viewpoint because, among other reasons, this condition frequently leads to death.

Although septic shock is a somewhat common clinical phenomenon, the mechanisms involved as well as the pathological changes remain poorly understood. For example, despite the treatment of bacterial infection, many patients deteriorate further, which may be due to clinical sequelae of hypotension with low systemic vascular resistance, renal insufficiency, adult respiratory distress syndrome, severe coagulopathy and severe metabolic dysfunctions. Thus, there is an urgent need in the art for effective methods of treating septic shock.

SUMMARY OF THE INVENTION

In accordance with the present invention, a method of treating septic shock in mammals includes administering a septic shock-treating effective amount of T$\alpha_1$ to said mammals.

DESCRIPTION OF THE PREFERRED EMBODIMENTS

It surprisingly has been discovered that Thymosin $\alpha_1$ (T$\alpha_1$) is effective in treating or preventing septic shock or sepsis in mammals. This discovery was surprising, because Thymosin $\alpha_1$ was expected to be without activity with respect to septic shock when initially tested.

The terms "Thymosin $\alpha_1$" and "T$\alpha_1$" refer to peptides having the amino acid sequence disclosed in U.S. Pat. No. 4,079,137, supra.

Mammalian septic shock occurs in association with a series of events in the mammal's body referred to as the "sepsis cascade". The sepsis cascade typically begins with bacterial infection of the mammalian host resulting in release of bacterial toxins, introduction of endotoxin, activation of host defense systems, i.e., plasma protein systems as well as cellular defense systems including endothelial cells, macrophages, monocytes and neutrophils, with release of proinflammatory mediators including cytokines, lipid metobolites, proteases, toxic oxygen products, nitric oxide and adhesion proteins.

According to one aspect of the present invention, effective amounts of T$\alpha_1$ are administered to a subject to reduce blood free radical levels in the subject, and thereby treat or prevent septic shock in the subject or obstruct progression of sepsis cascade in the subject. T$\alpha_1$ has been found to reduce blood free radical levels almost as much as SOD (super oxide dismutase), an enzyme that eliminates free radicals. When a septic shock-treating or a septic shock-preventing effective amount of T$\alpha_1$ is administered to a mammal, the blood levels of pathological mediators of bacteria-induced lethality are decreased in the mammal.

T$\alpha_1$ has been found to obstruct the sepsis cascade in mammals. During sepsis, peroxidation of lipids in blood is increased (mMol of malonyldialdehyde), but returned to normal or about normal with T$\alpha_1$ administration. Sepsis also reduces circulating blood leves of glutathione. However, administration of T$\alpha_1$ returns circulatory gluthathine leves to normal or about normal.

As noted above, administration of T$\alpha_1$ during sepsis decreases blood hydroperoxide levels and increases blood glutathione levels. Administration of T$\alpha_1$ during sepsis also decreases cerebellar cGMP levels, and decreases the blood levels of arachidonic acid metabolites such as Tx$\beta_2$ and 6-keto-PGF$_1\alpha$, PAF, and cytokines such as IL-1$\alpha$ and TNF-$\alpha$.

While not wishing to be bound to any particular theory, it is believed that reducing blood levels of pathological mediators of bacteria-induced lethality in a mammal decreases the amount of infection in the mammal which, in turn, aids in obstructing the spesis cascade, and in preventing and treating septic shock.

Thus, according to the present invention, methods of treating and preventing septic shock in mammals are provided. The methods of the present invention include administration of septic shock-treating effective amounts, septic shock-preventing effective amounts and sepsis cascade progression-obstructing effective amounts of T$\alpha_1$ to mammals.

According to preferred embodiments of the present invention, effective amounts of T$\alpha_1$ are administered to subjects to treat or prevent septic shock in the subjects, or obstruct progression of sepsis cascade in the subjects. In these embodiments, the subjects preferably are human.

According to preferred embodiments of the present invention, compositions containing T$\alpha_1$ may be formulated in a conventional manner for administration by any suitable route. Suitable routes of administration include, but are not limited to, oral, rectal, nasal, topical, vaginal, and parenteral (including subcutaneous, intramuscular, intravenous and intradermal). Particularly preferred embodiments utilize oral or parenteral administration, with parenteral administration being a more preferred embodiment. It will be appreciated that the preferred route may vary with the condition, age and species of the recipient.

While not essential, in preferred embodiments, $T\alpha_1$ is administered as part of a pharmaceutical formulation. The formulations of the present invention comprise $T\alpha_1$ together with one or more pharmaceutically acceptable carriers and optionally with other therapeutic ingredients. The carrier(s) are "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and may be prepared by any suitable pharmaceutical methods.

Such methods include, but are not limited to, the step of bringing into association $T\alpha_1$ with the carrier which constitutes one or more accessory ingredients. In general, the formulations are prepared by uniformly and intimately bringing into association $T\alpha_1$ with liquid carriers or finely divided solid carriers or both, and then, if necessary, shaping the product.

Formulations of the present invention suitable for oral administration may be presented as discrete units such as capsules, cachets or tablets each containing a predetermined amount of $T\alpha_1$, as a powder or granules; as a solution or a suspension in an aqueous liquid or a non-aqueous liquid; or as an oil-in-water liquid emulsion or a water-in-oil liquid emulsion, etc.

A tablet may be made by compression or molding, optionally with one or more accessory ingredients. Compressed tablets may be prepared by compressing in a suitable machine $T\alpha_1$ in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration include lozenges comprising $T\alpha_1$ in a flavored basis, usually sucrose and acacia or tragacanth; pastilles comprising $T\alpha_1$ in an inert basis such as gelatin and glycerin, or sucrose and acacia; and mouthwashes comprising $T\alpha_1$ to be administered in a suitable liquid carrier.

Formulations suitable for topical administration to the skin may be presented as ointments, creams, gels and pastes comprising $T\alpha_1$ and a pharmaceutically acceptable carrier, or may utilize a transdermal patch containing the ingredient to be administered.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range from about 20 to about 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for vaginal administration may be presented as tampons, creams, gels, pastes, foams or spray formulations containing, in addition to $T\alpha_1$, suitable carriers.

Formulations suitable for parenteral administration include aqueous and non-aqueous sterile injection solutions which may optionally contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other suitable agents having regard to the type of formulation in question, for example, those suitable for oral administration may include flavoring agents.

A dose for administration of the compositions in the present invention is a septic shock-treating or a septic shock-preventing effective amount of $T\alpha_1$, which can be in a range of from about 0.4 mg to about 4 mg of $T\alpha_1$ per kg of body weight of recipient (mg/kg), preferably from about 1 to about 4 mg/kg. A dose can be administered to the patient daily, one or more times per day of administration, e.g., two or three times per day, and doses can be administered one or more days per week, e.g., two, three, four, five, six or seven days per week.

The invention is applicable to native (i.e., naturally occurring) $T\alpha_1$, as well as synthetic $T\alpha_1$ and recombinant $T\alpha_1$ having the amino acid sequence of native $T\alpha_1$, amino acid sequences substantially similar thereto, or an abbreviated sequence form thereof, and their biologically active analogs (including muteins) having substituted, deleted, elongated, replaced, or otherwise modified sequences which possess bioactivity substantially similar to that of $T\alpha_1$.

In accordance with one embodiment of the present invention, $T\alpha_1$ can be administered in combination with a therapeutically effective amount of another substance useful in treating septic shock such as, for example, antibiotics, or antibodies (polyclonal or monoclonal) directed to antigens located on endotoxins. Of course, the acceptable dosage range of the other substance will depend upon its properties (i.e., the acceptable dosage range will depend upon what other substance is being administered).

$T\alpha_1$ and another substance useful in preventing or treating septic shock can be administered "in combination" which, as defined herein, includes various schemes designed to administer $T\alpha_1$ and the other substance to a subject, whether or not the other substance and $T\alpha_1$ are administered separately or together, such that the desired dosages of $T\alpha_1$ and the other substance are present in the subject at the same time. Any suitable scheme can be used to administer $T\alpha_1$ and another substance useful in preventing or treating septic shock "in combination" in accordance with the present invention.

Suitable dosages of either $T\alpha_1$ alone or $T\alpha_1$ in combination with another substance useful in treating or preventing septic shock may be administered 1 to 3 times or more per day. The precise dose administered will depend on the age, condition and other factors of the recipient.

The following examples are for illustrative purposes only, and are not to be construed in a limiting sense.

EXAMPLE 1

Synthetic $T\alpha_1$ was provided by Alpha 1 Biomedicals, Inc. (Two Democracy Center, 6903 Rockledge Drive, Ste. 1200, Bethesda, Md. 20817). $T\alpha_1$ was prepared by solid phase peptide synthesis.

Swiss-Webster mice 4–6 weeks of age (20–25 g) were divided into 2 groups: endotoxic mice (endotoxin 60 mg/kg i.p. in acute treatment) and endotoxic mice treated with 3 injections of 100 µg $T\alpha_1$ (5 minutes, 2 and 4 hours post administration of the endotoxin).

The results presented in Tables I and II below indicate that $T\alpha_1$ administered 3 times post administration of endotoxin increased the survival rate of mice treated with endotoxin to 100%.

The results presented in Tables III–VII below show effects of $T\alpha_1$ respectively on mice blood malonyldialdehyde levels, glutathione levels, cerebellar cGMP levels, blood serum TNF-α levels, and blood serum TNF-α and IL-1α levels.

TABLE I

Survival of Swiss Webster Mice Following Lethal Endotoxin Dose and $T\alpha_1$

| EXPERIMENTAL GROUPS | Number of Mice Alive | | | |
|---|---|---|---|---|
| | 0 hrs | 24 hrs | 48 hrs | 72 hrs |
| Endotoxin 60 mg/kg | 7 | 1 | 1 | 1 |
| Endotoxin 60 mg/kg + $T\alpha_1$ 100 µg 3× | 7 | 7 | 7 | 7 |

TABLE II

Protective Effect of $T\alpha_1$ on Survival of Mice Treated with Lethal Doses of Endotoxin

| EXPERIMENTAL GROUPS | Number of Mice Alive | | | | | |
|---|---|---|---|---|---|---|
| | 0 hr. | 24 hr. | 48 hr. | 72 hr. | 7 day | 14 day |
| Endotoxin 60 mg/kg | 8 | 0 | | | | |
| Endotoxin 60 mg/kg + $T\alpha_1$ 100 µg 3× | 8 | 8 | 8 | 8 | 8 | 8 |

TABLE III

The effects of $T\alpha_1$ on changes in blood hydroperoxide levels after treating the mice with lethal doses of endotoxin

| EXPERIMENTAL GROUPS | Blood levels of malonyldialdehyde (nMol MDA) |
|---|---|
| Control | 17.5 ± 1.2 |
| Endotoxin 60 mg/kg | 38.2 ± 2.9 |
| Endotoxin 60 mg/kg + $T\alpha_1$ 100 | 16.9 ± 1.36 |

*Whole blood samples (0.5 ml) were obtained by tail bleds 1 hour after endotoxin administration

TABLE IV

The effects of $T\alpha_1$ gluthathione levels in mice treated with lethal doses of endotoxin

| EXPERIMENTAL GROUPS | RBC GSH (µmoles/ml cells)* |
|---|---|
| Control | 1.25 ± 0.09 |
| Endotoxin 60 mg/kg | 0.61 ± 0.05 |
| Endotoxin 60 mg/kg + $T\alpha_1$ 100 µg/mouse | 1.12 ± 0.12 |

*Total erythrocyte glutathione, 98% of which is in the reduced form (GSH), was determined by the enzymatic "cyclic method."

TABLE V $T\alpha_1$ effects on cGMP cerebellar levels in mice treated with lethal doses of endotoxin

| EXPERIMENTAL GROUPS | Cerebellar cortex cyclic GMP (pmol per mg/protein) |
|---|---|
| Control | 10.1 ± 0.2 |
| Endotoxin 60 mg/kg i.p. | 30.7 ± 4.1 |
| Endotoxin 60 mg/kg i.p. + $T\alpha_1$ 100 µg | 14.6 ± 1.2 |

TABLE VI

Serum TNF-α levels in mice treated with lethal doses of endotoxin

| EXPERIMENTAL GROUPS | TNF-α (pg/ml) | | |
|---|---|---|---|
| | 1 hr | 3 hr | 5 hr |
| Endotoxin 60 mg/kg | 1098 ± 106 | 783 ± 38 | 623 ± 51 |
| Endotoxin 60 mg/kg + $T\alpha_1$ | 638 ± 57 | 426 ± 37 | 297 ± 27 |

TABLE VII

Serum TNF-α and IL-1α levels* in mice protected against endotoxin-induced lethality by pretreatment with SOD and $T\alpha_1$

| Pretreatment | TNF-α (pg/ml) | IL-1 α (pg/ml) |
|---|---|---|
| None | 4462 ± 123 | 1137 ± 123 |
| SOD (3.3 × 10⁴ µ/kg) | 63 ± 5.1 | 53 ± 3.1 |
| $T\alpha_1$ 100 µg/mice | 285 ± 23.6 | 109 ± 71 |

*Mice were pretreated with SOD (super oxide dismatase), 30 minutes before endotoxin administration XX blood for determined of TNFα and IL-1α levels was collected 1 hr after endotoxin administration.

EXAMPLE 2

Using the same materials and methods as in example 1, the time and dose-dependency of the protective effect of $T\alpha_1$ on endotoxin lethality were studied. The results are presented in Table VIII below.

As can be seen in Table VIII, $T\alpha_1$ had protective effect on endotoxin toxicity when given immediately following, 2 and 4 hours after endotoxin treatment or when given 2, 4 and 6 hours after endotoxin treatment. The effective protective dose was 100 µg $T\alpha_1$ administered three times.

TABLE VIII

Survival of Swiss Webster Mice Following Lethal Endotoxin Dose and $T\alpha_1$

| Experimental Groups | Number of Mice Alive | | | | | |
|---|---|---|---|---|---|---|
| | 0 hrs | 24 hrs | 48 hrs | 72 hrs | 96 hrs | 120 hrs |
| Endotoxin 60 mg/kg | 8 | 4 | 4 | 4 | 4 | 4 |
| Endotoxin 60 mg/kg + $T\alpha_1$ 100 µg, 3×; $T\alpha_1$ was administered immediately following, 2 and 4 hrs. after endotoxin. | 8 | 8 | 8 | 8 | 8 | 8 |
| Endotoxin 60 mg/kg + $T\alpha_1$ 100 µg, 3×; $T\alpha_1$ was administered 2, 4 and 6 hrs. after endotoxin. | 8 | 8 | 8 | 8 | 8 | 8 |
| Endotoxin 60 mg/kg + $T\alpha_1$ 10 µg, 3×; $T\alpha_1$ was administered immediately following, 2 and 4 hrs. after endotoxin. | 8 | 8 | 5 | 5 | 5 | 5 |

EXAMPLE 3

Using the same methods and materials as in examples 1 and 2, the effect which $T\alpha_1$ has on blood levels of IL-1α, TNF-α, PAG, $Tx\beta_2$ and 6-keto-$PGF_1\alpha$, which are pathological mediators of endotoxin induced lethality, was studied. The results are presented in Tables IX–XIV below.

As can be seen in Tables IX–XIV, $T\alpha_1$ decreased IL-1α, TNF-α serum levels as well as PAF, $Tx\beta_2$ and 6-keto-$PGF_1\alpha$ plasma levels after administration of a lethal dose of endotoxin.

TABLE IX

| EXPERIMENTAL GROUPS | IL-1α pg/ml (serum levels) | |
|---|---|---|
| | 1 hr | 3 hr |
| Endotoxin 60 mg/kg | 492 ± 45.2 | 550 ± 37.1 |
| Endotoxin 60 mg/kg + $T\alpha_1$ 100 µg administered immediately following | 83 ± 7.1 | 165 ± 13.7 |

TABLE X

| EXPERIMENTAL GROUPS | PAF (pg/ml) (plasma levels) | | | |
|---|---|---|---|---|
| | 0.5 hr | 1 hr | 2 hr | 3 hr |
| Endotoxin 60 mg/kg | 78 ± 6 | 279 ± 17 | 127 ± 13 | 55 ± 3 |
| Endotoxin 60 mg/kg + $T\alpha_1$ 100 µg administered immediately following | 48 ± 3 | 136 ± 9 | 68 ± 4 | 32 ± 2 |

TABLE XI

| EXPERIMENTAL GROUPS | $T \times \beta_2$ (pg/ml) (plasma levels) | | | |
|---|---|---|---|---|
| | 0.5 hr. | 1 hr | 2 hr | 3 hr |
| Endotoxin 60 mg/kg | 1442 ± 103 | 2937 ± 258 | 912 ± 105 | 695 ± 65 |
| Endotoxin 60 mg/kg + $T\alpha_1$ 100 µg administered immediately following | 910 ± 85 | 1921 ± 185 | 530 ± 47 | 391 ± 260 |

TABLE XII

| EXPERIMENTAL GROUPS | 6-keto-PGF1α (pg/ml) (plasma levels) | | | |
|---|---|---|---|---|
| | 0.5 hr. | 1 hr | 2 hr | 3 hr |
| Endotoxin 60 mg/kg | 341 ± 31 | 1141 ± 112 | 897 ± 75 | 811 ± 7 |
| Endotoxin 60 mg/kg + $T\alpha_1$ 100 µg administered immediately following | 224 ± 19 | 745 ± 62 | 341 ± 33 | 205 ± 19 |

TABLE XIII

| EXPERIMENTAL GROUPS | PAF (pg/ml) (serum levels) | | |
|---|---|---|---|
| | 1 hr | 3 hr | 5 hr |
| Endotoxin 60 mg/kg | 938 | 662 | 567 |
| Endotoxin 60 mg/kg + $T\alpha_1$ 100 µg administered immediately following | 783 | 508 | 429 |

TABLE XIV

| EXPERIMENTAL GROUPS | TNF-α (pg/ml) (serum levels) | | |
|---|---|---|---|
| | 1 hr | 3 hr | 5 hr |
| Endotoxin 60 mg/kg | 938 | 662 | 567 |
| Endotoxin 60 mg/kg + T$\alpha_1$ 100 μg administered immediately following | 783 | 508 | 429 |

EXAMPLE 4

Using a septic shock model in rats (Sprague-Dawley, male, 200–225 g each), the effect of thymosin $\alpha_1$ alone and together with antibiotics was studied. Peritonitis was induced in rats in the following way. A 1-cm incision was made into the peritoneal which exposed the cecum. A tight ligature was placed around the cecum with 4-0 suture distal to the insertion of the small bowel, forming an area of devitalized tissue while maintaining bowel continuity. A puncture wound was made with 16-gauge needle into the anti-mesenteric surface of the cecum and a small amount of fecal contents was expressed through the wound. The cecum was replaced into the peritoneal cavity, and the anterior peritoneal wall and skin were closed with surgical staples. Each animal was given a bolus of normal saline (15 ml/kg) for hydration and allowed to recover overnight.

The results presented in Table XV show T$\alpha_1$ increased the survival of rats.

TABLE XV

Survival of Sprague-Dawley rats following septic shock, antibiotics, and thymosin $\alpha_1$

| EXPERIMENTAL GROUPS | 0 hr | 24 hr | 48 hr | 72 hr |
|---|---|---|---|---|
| Rats with peritonitis + antibiotic* | 10 | 1 | 1 | 0 |
| Rats with peritonitis + antibiotic* + thymosin $\alpha_1$ 1 mg/rat × 3** | 10 | 8 | 6 | 6 |

*gentamicin sulfate, 1 mg/rat
**At 0 hr, 2 hr, and 4 hr post induction of peritonitis The results presented in Tables XVI to XIX below show effects of T$\alpha_1$ respectively on rat cytokine levels, blood malonyldialdehyde levels, glutathione levels and arachidonic acid metabolic levels.

TABLE XVI

The effect of T$\alpha_1$ on Cytokine Levels in a septic shock model in rat

| EXPERIMENTAL GROUPS | TNFα (pg/ml) | IL$_1$α (pg/ml) |
|---|---|---|
| Control | undetectable | undetectable |
| Rats with Septic Shock | 2658 ± 197 | 1387 ± 123 |
| Rats with Septic Shock + T$\alpha_1$ 1 mg/rat × 3 as above | 1231 ± 129 | 689 ± 53 |

TABLE XVII

The effect of T$\alpha_1$ on lipid peroxidation in a septic shock model in rat

| EXPERIMENTAL GROUPS | Blood Levels of malonyl-dialdehyde (nNol MDA) | |
|---|---|---|
| Control | 15.3 ± 1.3 | 18.6 ± 1.1 |
| Rats with Septic Shock | 49.1 ± 3.5 | 46.3 ± 3.8 |
| Rats with Septic + T$\alpha_1$ 1 mg/rat × 3 as above | 17.1 ± 1.6 | 21.9 ± 2.3 |

TABLE XVIII

The effect of T$\alpha_1$ on glutathione levels in a rat septic shock model

| EXPERIMENTAL GROUPS | RBC GSH (μmoles/ml cells) | |
|---|---|---|
| Control | 1.38 ± 0.1 | 1.46 ± 0.13 |
| Rats with Septic Shock | 0.43 ± 0.05 | 0.29 ± 0.04 |
| Rats with Septic Shock + T$\alpha_1$ mg/rat × 3 as above | 1.29 ± 0.07 | 1.20 ± 0.085 |

TABLE XIX

The effect of T$\alpha_1$ on arachidonic acid metabolite levels in a septic shock model in rat

| EXPERIMENTAL GROUPS | 6-keto-PGF$_1$ (pg/ml) | T × β$_2$, (pg/ml) |
|---|---|---|
| Control | 58 ± 3.5 | 89 ± 7.6 |
| Rats with Septic Shock | 1828 ± 145.3 | 3622 ± 295 |
| Rats with Septic Shock + T$\alpha_1$ 1 mg/rat × 3 as above | 1132 ± 96 | 2353 ± 197 |

The results presented in Tables XX and XXI below demonstrate that T$\alpha_1$ increases the survival rate of rats with septic shock.

TABLE XX

| EXPERIMENTAL GROUPS | Number of Rats Alive | | | |
|---|---|---|---|---|
| | 0 h | 24 h | 48 h | 72 h |
| Rats with Septic Shock | 10 | 2 | 2 | 0 |
| Rats with Septic Shock + T$\alpha_1$ 1 mg/rat × 3 as above | 10 | 9 | 9 | 5 |

TABLE XXI

| EXPERIMENTAL GROUPS | Number of Rats Alive | | | |
|---|---|---|---|---|
| | 0 h | 24 h | 48 h | 72 h |
| Rats With Septic Shock | 10 | 1 | 0 | 0 |
| Rats with Septic Shock + T$\alpha_1$ 1 mg/rat × 3 as above | 10 | 8 | 7 | 3 |

While the invention has been described and illustrated with details and references to certain preferred embodiments, those skilled in the art will appreciate that various modifications, changes, omissions, and substitutes can be made without departing from the spirit of the invention.

What is claimed is:

1. A method of reducing toxicity of endotoxin in a mammal following endotoxin introduction in said mammal, comprising administering to said mammal an endotoxin-reducing effective amount of $T\alpha_1$.

2. The method of claim 1, wherein said amount of $T\alpha_1$ is sufficient to reverse in said mammal at least one member selected from the group consisting of increased cerebellar cGMP levels, increased blood malonyldialdehyde levels, decreased blood glutathione levels, increased blood PAF levels, increased blood $Tx\beta_2$ levels, increased blood 6-keto-$PGF_1\alpha$ levels, increased blood IL-1$\alpha$ levels and increased blood TNF$\alpha$ levels.

3. A method of treating endotoxin-associated bacterial infection in a mammal which comprises administering to said mammal an endotoxin-associated bacterial infection-treating effective amount of $T\alpha_1$.

4. The method of claim 3, wherein said amount of $T\alpha_1$ is sufficient to reverse in said mammal at least one member selected from the group consisting of increased cerebellar cGMP levels, increased blood malonyldialdehyde levels, decreased blood glutathione levels, increased blood PAF levels, increased blood $Tx\beta_2$ levels, increased blood 6-keto-$PGF_1\alpha$ levels, increased blood IL-1$\alpha$ levels and increased blood TNF$\alpha$ levels.

* * * * *